United States Patent [19]

Scheuer et al.

[11] Patent Number: 5,767,249
[45] Date of Patent: Jun. 16, 1998

[54] MONOCLONAL ANTIBODIES AGAINST TYPE I PHOSPHOLIPASE $A_2$ AS A DIAGNOSTIC AND ANTI-INFLAMMATORY THERAPEUTIC AGENT

[75] Inventors: Werner Scheuer, Penzberg; Christa Hübner-Parajsz, Tutzing; Ulrich Tibes, Frankfurt, all of Germany

[73] Assignee: Boehringer Mannheim GmbH, Mannheim, Germany

[21] Appl. No.: 512,509

[22] Filed: Aug. 8, 1995

Related U.S. Application Data

[63] Continuation of Ser. No. 262,144, Jun. 20, 1994, abandoned.
[51] Int. Cl.[6] .................. C07K 16/40; A61K 39/395
[52] U.S. Cl. .................. 530/388.26; 530/388.25; 424/130.1; 424/140.1
[58] Field of Search .................. 424/130.1, 140.1; 530/388.26, 388.25

[56] References Cited

U.S. PATENT DOCUMENTS 5,244,789  9/1993  Neumann et al. .

FOREIGN PATENT DOCUMENTS 0287397  10/1988  European Pat. Off. .
0459450  12/1991  European Pat. Off. .

OTHER PUBLICATIONS

Misaki et al., Production and Cahracterization of Monoclonal Antibodies against Human Pancreatic Phospholipase A2. J.Clin. Biochem. Nutr. vol. 11, pp. 79–89, 1991.
Waldmann, Monoclonal Antibodies in Diagnosis and Therapy, Science, vol. 252, 1657–1662, 1991.
Takamaya et al., "Monoclonal Antibodies Against Human Synovial Phospholipase A2", Biochemical and Biophysical Research Communications, vol. 167, No. 3, pp. 1309–1315 (1990).

Primary Examiner—Toni R. Scheiner
Attorney, Agent, or Firm—Felfe & Lynch

[57] ABSTRACT

The invention provides for monoclonal antibodies which specifically bind to type I phospholipase $A_2$ for use as a diagnostic agent and as an anti-inflammatory therapeutic agent, which is particularly suitable for application in acute pancreatitis. The invention further provides for pharmaceutical compositions including the antibodies of the invention. The invention also provides for a method for treating subjects suffering from inflammatory symptoms and for detecting the activity of type I phospholipase $A_2$ in a sample.

5 Claims, 1 Drawing Sheet

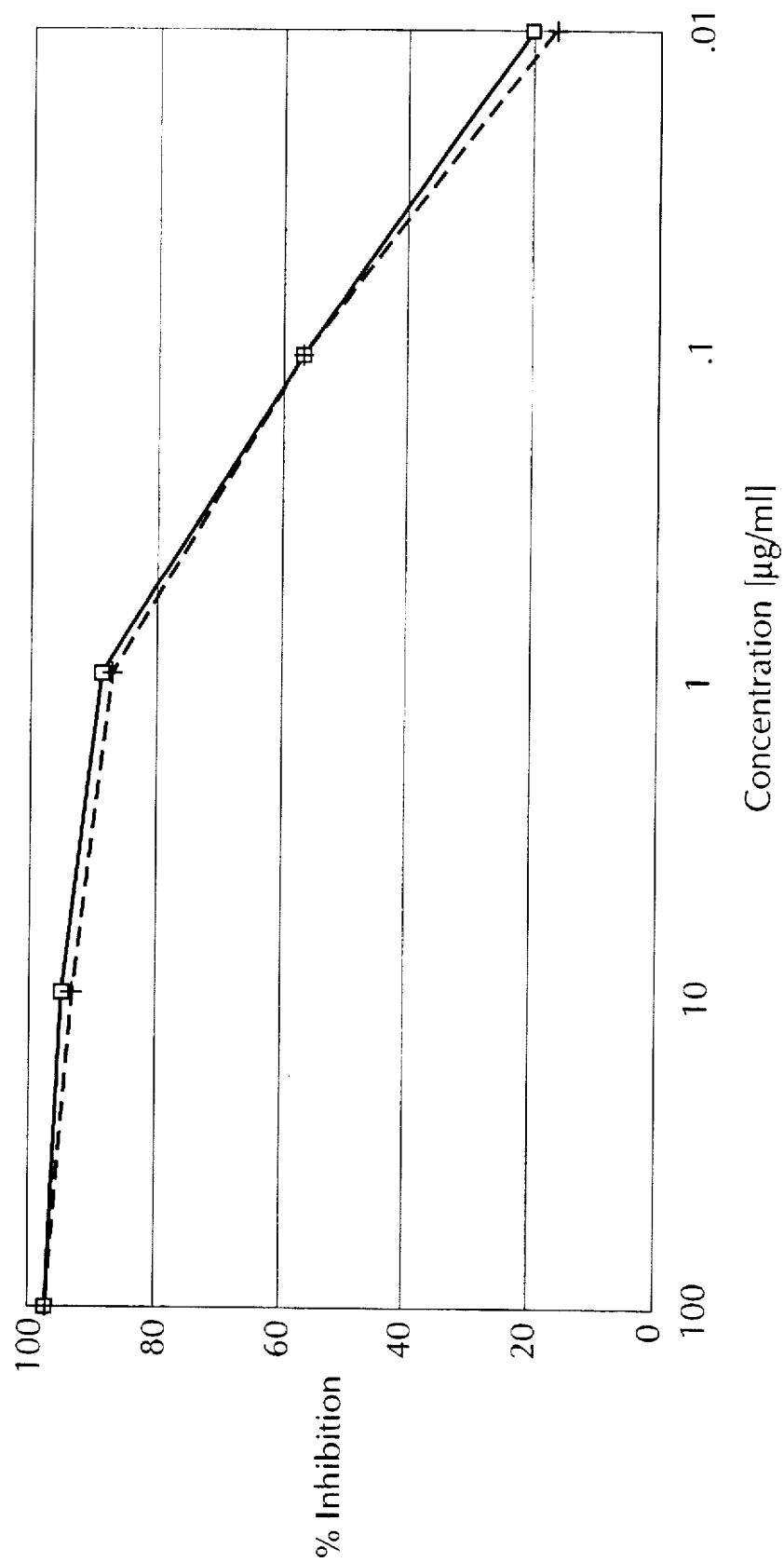

MONOCLONAL ANTIBODIES AGAINST TYPE I PHOSPHOLIPASE $A_2$ AS A DIAGNOSTIC AND ANTI-INFLAMMATORY THERAPEUTIC AGENT

RELATED APPLICATIONS

This application is a continuation of application Ser. No. 08/262,144, filed Jun. 20, 1994, now abandoned, which is a continuation-in-part application of International Application PCT/EP92/02905, with an International filing date of Dec. 15, 1992.

FIELD OF THE INVENTION

The invention concerns the use of monoclonal antibodies against type I phospholipase $A_2$ for the production of an anti-inflammatory therapeutic agent which is particularly suitable for application in acute pancreatitis.

BACKGROUND OF THE INVENTION

There is neither a causal nor symptomatic therapy for acute pancreatitis (The Merck Manual of Diagnosis and Therapy 15 (1987), pages 763–767). The pathogenetic basis of acute pancreatitis is autolysis of the pancreas. Phospholipase $A_2$ has been attributed a decisive function in this process. It has a lysing action on the cell membrane and liberates arachidonic acid from the membrane phospholipids in this process. The metabolites of arachidonic acid (prostaglandins and leukotrienes) are an important component of the inflammatory reaction.

Phospholipase $A_2$ occurs in two forms. The phospholipase $A_2$ designated type I is mainly found in pancreatic tissue and plays an important role in acute pancreatitis. In contrast type II phospholipase $A_2$ occurs in many different tissues.

Low-molecular inhibitors of phospholipase $A_2$ are described in EP-A 0 248 597 which have an anti-inflammatory action in the mouse. However, administration of 200–400 μg of these compounds is necessary for an approximately 80% inhibition. At such high doses, the side effects of these low-molecular inhibitors significantly limit their therapeutic applicability. The inhibitor of phospholipase $A_2$ described in JP 088193 for which a daily dose of 100–1000 mg is proposed for pancreatitis therapy in adult patients also has this disadvantage. The phospholipase $A_2$ inhibitors described in EP-A 0 405 864 from the microorganism *Circinotrichum falcatisporum* have $IC_{50}$ values for the inhibition of purified rat phospholipase $A_2$ of 17.5 to more than 300 μg/ml and therefore also would have to be used in very high doses for a therapeutic application.

Another inhibitor of phospholipase $A_2$ which also has an anti-inflammatory action is the 37 kD lipocortin (B. Wallner et al., Nature 320 (1986), 77–81). However, due to its low stability lipocortin is not suitable for therapeutic use. Hence peptides of 15–26 amino acids in size are described in EP-A 0 327 334 which have an inhibitory effect on phospholipase $A_2$. However, only one of these peptides has an $IC_{50}$ value below 10 μg/ml. It is however, not demonstrated that this peptide of 16 unprotected amino acids has a higher stability than lipocortin.

Monoclonal antibodies against human phospholipase $A_2$ from synovial fluid are described by K. Takayama et al. (Biochem. Biophys. Res. Comm. 167 (1990), 1309–1315) which, however, do not bind to phospholipase $A_2$ from the pancreas.

Monoclonal antibodies against phospholipase $A_2$ from the pancreas are described in EP-A 0 287 397 and J. Clin. Biochem. Nutr. 11 (1991), 79–89. Some of these antibodies inhibit the enzymatic activity of phospholipase $A_2$ with an $IC_{50}$ of 0.2 ng/ml. However, only a diagnostic use of these antibodies is described.

SUMMARY OF THE INVENTION

This invention provides for an inhibitor for phospholipase $A_2$ whose inhibitory effect enables the use of this inhibitor as a diagnostic agent and a therapeutic agent for inflammatory reactions, e.g., acute pancreatitis.

The invention is achieved by the use of monoclonal antibodies against type I phospholipase $A_2$ which cause an at least 50% inhibition of the activity of phospholipase $A_2$ at a concentration of less than 100 ng/ml, or of functional fragments of these antibodies, for the production of a therapeutic agent which can be used for inflammatory symptoms and especially for acute pancreatitis.

It surprisingly turned out that it is possible to obtain a particularly efficient therapeutic agent for inflammatory reactions in particular for acute pancreatitis, psoriasis, peritonitis or sepsis using a monoclonal antibody against type I phospholipase $A_2$ or a functional derivative of such an antibody. In addition to the complete antibodies, functional antibody fragments such as monoclonal Fab or F(ab') fragments as well as divalent F(ab')$_2$ fragments are also suitable for this.

The invention therefore also concerns a pharmaceutical formulation comprising a monoclonal antibody against type I phospholipase $A_2$ or a functional derivative of this antibody, if desired, together with the usual pharmaceutical carrier substances, fillers, auxiliary substances and additives, as well as a process for the production of such a pharmaceutical agent which can be in particular used for the therapy of acute pancreatitis.

The monoclonal antibodies of the invention may also be used as a diagnostic tool to detect $PLA_2$ activity.

The monoclonal antibodies obtainable from the hybridoma lines DSM ACC2026 and DSM ACC2025 have proven to be particularly suitable for the use according to the invention.

A further preferred subject matter of the invention therefore in addition concerns monoclonal antibodies against type I phospholipase $A_2$ which are capable of binding in an equivalent manner to type I phospholipase $A_2$ as the monoclonal antibodies against type I phospholipase $A_2$ obtainable from the cell lines DSM ACC2026 and/or DSM ACC2025.

BRIEF DESCRIPTION OF THE FIGURE

FIG. 1 shows the inhibition of phospholipase $A_2$ activity of the monoclonal antibodies DSM ACC2026 (+) and DSM ACC2025 (□).

DETAILED DESCRIPTION OF THE EMBODIMENT

The term "antibodies capable of binding in an equivalent manner" denotes antibodies in which an epitope overlap with the defined known antibody can be detected. This epitope overlap can be determined with the aid of a competitive test system. For this an enzyme immunoassay is used, for example, to examine to what extent an antibody competes with the known antibody for binding to a defined antigen or a special epitope. For this, the appropriate antigen is incubated with the known monoclonal antibody in a labelled form and an excess of the antibody under consideration. It can then easily be determined by immobilizing the complexes formed, separating the solid from the liquid phase and detecting the bound label in one of the two phases, to what extent the antibody under consideration can displace the defined antibody from the binding. If there is a displacement of at least 50% at a $10^5$-fold excess, then an epitope overlap is present.

The monoclonal antibodies against type I phospholipase $A_2$ which can be obtained from the cell lines DSM ACC2026 and/or DSM ACC2025 are particularly preferred.

The invention in addition concerns the cell lines DSM ACC2026 and/or DSM ACC2025.

The monoclonal antibodies according to the invention are obtainable by immunizing with purified phospholipase $A_2$, immortalizing spleen cells of the immunized animals and cloning those immortalized cells whose culture supernatant contains an antibody which causes an inhibition of the activity of phospholipase $A_2$ with an $IC_{50}$ of less than 100 ng/ml. The monoclonal antibodies produced by these clones are then isolated according to known methods.

The immunization is carried out in the animals which are usually used for this such as e.g. mice or rats. Mice are preferably used.

The immortalization of the spleen cells of the immunized animals is preferably carried out by fusing with the myeloma cell line P3X63-Ag 8.653 (ATCC CRL 1580) according to the method in J. of Imm. Meth. 39 (1980), 285–308. However, in addition other methods known to a person skilled in the art can also be used to immortalize the spleen cells.

For the cloning, the cells are example separated by means of a fluorescence-activated cell sorter. In order to detect immortalized cells which produce the desired antibody against phospholipase $A_2$, a sample of the culture supernatant is tested in an ELISA test for reactivity with phospholipase $A_2$. In order to obtain those antibodies which inhibit the enzymatic activity of phospholipase $A_2$, the culture supernatant of those clones which produce antibodies that bind to phospholipase $A_2$ is additionally examined for inhibition of phospholipase $A_2$ activity in an enzymatic test.

Those clones whose culture supernatant shows the desired inhibition of phospholipase $A_2$ activity are expanded and the antibodies produced by these clones are isolated according to known methods.

The hybridoma cell lines DSM ACC2026 and DSM ACC2025 which produce a monoclonal antibody according to the invention against phospholipase $A_2$ were deposited on 10.12.1991 at the "Deutsche Sammlung von Zelkulturen und Mikroorganismen GmbH", Mascheroder Weg 1b, D-3300 Braunschweig.

The monoclonal antibodies which inhibit type I Phospholipase $A_2$ $PLA_2$ can also be used as a differential diagnostic agent. $PLA_2$ can be measured in a nonimmunoassay with or without the antibody according to the invention. From the difference of the results, the amount of pancreatic $PLA_2$ in the sample can be calculated. It is preferred to use the monoclonal antibodies in a concentration for complete inhibition (about or more than 90%). Useful amounts of the monoclonal antibodies are therefore about 10 to 100 µg/ml, or preferably about 100 µg/ml. $PLA_2$ belongs to a family of regulatory enzymes which controls the synthesis of eicosanoids and the platelet aggregating factor (PAF). It has been demonstrated with respect to a large number of diseases that an increased $PLA_2$ serum activity correlates with the degree of severity of the diseases. (Vadas, P. et al., Lab. Invest. 55: 391–399 (1986), Anderson et al., J. Surg. Res. 56: 199–205 (1994)).

Thus the determination of $PLA_2$ activity may be used as a diagnostic and prognostic marker (Vadas et al., J. Lab. Clin. Med 104: 873–881, (1984), Buchler, M. et al., Klin Wochenschrift 67: 186–189 (1989) and Ogawa, M. et al., Res. Comm. Chem. Pathol. Pharmacol. 75: 109–115 (1992)). There are tests which determine the catalytic activity of the enzyme, applying a colorimetric test that quantifies the free fatty acids formed (Hoffman, G. E. et al., J. Clin. Chem. Clin. Biochem 24: 871–875 (1986), or a radiochemical test using as a substrate, a radioactively-labelled *E. coli* membrane (Aufenanger, J., et al., Clin. Chem. 39: 605–613, (1993). Both of these tests are unable to distinguish between two isoforms (type I $PLA_2$, pancreatic $PLA_2$; type II $PLA_2$; secretory $PLA_2$). According to recent data, type II $PLA_2$ plays a decisive role in induction and manifestation of the inflammatory process (Ogawa, et al., (1992) and Green, J. A. et al., Inflammation 15: 355–367 (1991)).

The invention is elucidated by the following examples in conjunction with FIG. 1 and will be better understood by reference to the following examples, which are included here for purposes of exemplification and are not to be construed as limitation.

EXAMPLE 1

Production of monoclonal antibodies against type I phospholipase $A_2$.

12 week old Balb/c mice are immunized intraperitoneally with 50 µg purified phospholipase $A_2$ (EC 3.1.1.4, V. Kozumplik et al., Biochim. Biophys. Acta 1002 (1989), 395–397) in complete Freund's adjuvant. Two subsequent injections of 50 µg in each case are administered with incomplete Freund's adjuvant at intervals of one month in each case. 3 days before cell fusion, a further 50 µg in physiological saline is injected intravenously.

The fusion of the spleen cells of the immunized mice with the myeloma cell line P3X63-Ag 8.653 (ATCC CRL 1580) is carried out according to a modification of the method originally described by Köhler and Milstein (J. of Imm. Meth. 39 (1980), 285–308). The fused cells are cultured in RPMI 1640 medium (which contains 10% FCS, 2 mmol/l L-glutamine and 1 mmol/l sodium pyruvate as well as 0.1 mmol/l hypoxanthine and 10 µmol/l azaserine).

Positive primary cultures (determined according to examples 2 and 3) are cloned 2 weeks after fusion with the aid of a fluorescence-activated cell sorter. In this process the cells are deposited individually in 96-well microtitre plates.

Hybridoma cell lines identified as DSM ACC 2025 and DSM 2026 (their accession numbers) were produced using this method and were deposited at the Deutsche Sammlung von Zellkulturen und Microorganismen GmbH, Mascheroder Weg 1b, D-3300 Braunschweig, Germany, on December 10, 1991. The deposits were made in accordance with the Budapest Treaty, and 37 C.F.R. § 1.801–1.809.

EXAMPLE 2

Determination of the specificity of the antibodies produced

An enzyme-linked immunosorbent assay (ELISA) is used to determine the specificity of the antibodies in the culture supernatant of the hybridoma cells.

For this, 96-well microtitre plates are coated with 100 µl phospholipase $A_2$ antigen (5 µg/ml in carbonate buffer, Boehringer Mannheim GmbH, Catalogue No. 726 559), incubated for 2 hours at room temperature with 100 µl culture supernatant (diluted 1:25 with PBS (according to Dulbecco and Vogt, J. Exp. Meth. 99 (1954), 167–182) and washed with 3×350 µl PBS/0.05% Tween 20. After addition of the sample solution containing the antibody, it is incubated for one hour at room temperature and again washed. Afterwards it is incubated with POD-labelled sheep anti-mouse immunoglobulin G (10 mU, Boehringer Mannheim GmbH, Catalogue No. 13 77 377) for 1 hour at room temperature, washed with 3×350 µl PBS/0.05% Tween 20 and the detection reaction is started by addition of 100 µl ABTS® (1 mg/ml, Boehringer Mannheim GmbH, Catalogue No. 756 407) in 40 mmol/l citrate buffer pH 4.4 containing 3.25 mmol/l sodium perborate (Boehringer Mannheim GmbH, Catalogue No. 1204 530). The absorbance is determined at 405 nm in an ELISA reader after 30 minutes incubation at room temperature.

EXAMPLE 3

Test for the inhibition of enzymatic activity

Human duodenal phospholipase $A_2$ (s. example 1) is diluted with Tris buffer from the test combination "free fatty acids" (Boehringer Mannheim GmbH, Catalogue No. 1056 239). 20 µl of this enzyme solution is incubated for 15 minutes at 25° C. with 10 µl of the antibody solution to be examined in various concentrations (s. Table 1). Subsequently 20 µl substrate (lecithin emulsion from the test combination "free fatty acids", Boehringer Mannheim GmbH, Catalogue No. 1056 239) is added and incubated for 60 minutes at 37° C. The fatty acids released in this process by phospholipase $A_2$ activity are quantified by means of the test combination "free fatty acids" (Boehringer Mannheim GmbH, Catalogue No. 1383 175) by measuring the absorbance according to the manufacturer's instructions. The results are shown in the following Table 1 and in FIG. 1 as % inhibition in comparison to the enzymatic activity without antibodies (in each case the mean of 3 determinations).

TABLE 1

| Sample | Concentration (µg/ml) | % inhibition |
|---|---|---|
| DSM ACC2025 | 100 | 97 |
|  | 10 | 93 |
|  | 1 | 86 |
|  | 0.1 | 56 |
|  | 0.01 | 16 |
| DSM ACC2026 | 100 | 97 |
|  | 10 | 94 |
|  | 1 | 88 |
|  | 0.1 | 56 |
|  | 0.01 | 26 |

EXAMPLE 4

Determination of the epitope overlap of antibodies against phospholipase $A_2$

A competitive enzyme immunoassay is carried out in order to detect the epitope overlap of an antibody with the moncloneal antibody DSM DSM ACC2026.

For this, phospholipase $A_2$ is firstly biotinylated with D-biotinyl-ε-amido caproic acid-N-hydroxysuccinimide ester (Boehringer Mannheim GmbH, Catalogue No. 1008 960) according to the instructions of the manufacturer. 300 ng of this biotinylated antigen in a volume of 100 µl PBS is bound to a streptavidin-coated microtitre plate (manufactured according to EP-A 0 344 578) by one hour incubation at room temperature. After washing four times with PBS/0.05% Tween 20, it is simultaneously incubated for 90 minutes at room temperature with the monoclonal antibody DSM ACC 2025 or DSM ACC 2026 which has been labeled with peroxidase (final concentration of 250 mU/ml) and with the antibody under assessment. After washing again four times with PBS/0.05% Tween 20, it is incubated for 30 minutes at room temperature with the enzyme substrate solution ABTS® in buffer containing sodium perborate (s. example 2) and subsequently the absorbance at 405 nm is measured as a measure of the amount of bound POD-labelled monoclonal antibody DSM ACC2025 or DSM ACC2026. This value is compared with the absorbance which is obtained on incubation with the monoclonal antibody DSM ACC2025 or DSM ACC2026 alone. When a competition of at least 50% is observed at a $10^5$-fold excess of the antibody under assessment compared to the monoclonal antibody DSM ACC2025 or DSM ACC2026 as an enzyme conjugate (250 mU/ml), then an epitope overlap is present.

EXAMPLE 5

Inhibition of type I $PLA_2$-induced $PGE_2$ and $LTC_4$ release by human leucocytes in the presence of a monoclonal antibody against phospholipase $A_2$ Human leucocytes are isolated by density centrifugation (lymphocyte separation medium from Boehringer Mannheim GmbH, Cat. No. 295949) from peripheral blood and adjusted to a cell titre of $0.75 \times 10^6$ cells/ml in 125 mmol/l Tris buffer from the test combination "free fatty acids" (Boehringer Mannheim GmbH, Catalogue No. 1056 239). Various concentrations of purified human phospholipase $A_2$ (see example 1 and Table 2) are incubated for 4 hours at 37° C. with a solution of the monoclonal antibody DSM ACC2026 (concentration see Table 2) and the human leucocyte. Subsequently the cells are centrifuged for 10 minutes at 800 g and the $PGE_2$ and $LTC_4$ concentration is determined in the supernatant by a radioimmunoassay (Biermann, Bad Nauheim, Germany for $PGE_2$ and NEN DuPont, Dreieich, Germany for $LTC_4$). The results of two independent experiments in each case (human leucocytes from two different donors) are given in the following Table 2 (in each case means of three determinations). In the positive control mixtures (incubation with phospholipase $A_2$ type I, but without monoclonal antibody against this phospholipase $A_2$) the $PLA_2$-induced stimulation of the release of the inflammatory mediators $PGE_2$ and $LTC_4$ by human peripheral lymphocytes can be clearly seen. This release of $PGE_2$ and $LTC_4$ which in vivo leads to an inflammatory reaction can be substantially inhibited by addition of a monoclonal antibody against type I phospholipase $A_2$.

TABLE 2

| $PLA_2$ | MAB <$PLA_2$> | $PGE_2$ [ng/ml] | | $LTC_4$ [ng/ml] | |
|---|---|---|---|---|---|
| type I | DSM ACC2026 | exp. 1 | exp. 2 | exp. 1 | exp. 2 |
| — | — | 0.82 | 1.99 | 0.17 | 0.19 |
| 1 mg/ml | — | 5.42 | 9.13 | 0.87 | 0.91 |
| " | 0.1 mg/ml | 2.18 | 4.13 | 0.24 | 0.25 |
| " | 0.01 mg/ml | 3.23 | 5.20 | 0.31 | 0.28 |
| " | 0.001 mg/ml | 4.72 | 8.89 | 0.49 | 0.77 |
| 0.1 mg/ml | — | 2.16 | 4.44 | 0.23 | 0.32 |
| " | 0.1 mg/ml | 0.97 | 2.53 | 0.17 | 0.20 |
| " | 0.01 mg/ml | 1.29 | 2.74 | 0.16 | 0.19 |
| " | 0.001 mg/ml | 1.63 | 3.13 | 0.21 | 0.17 |
| 0.01 mg/ml | — | 1.05 | 2.44 | 0.17 | 0.15 |
| " | 0.1 mg/ml | 0.74 | 2.17 | 0.13 | 0.13 |

TABLE 2-continued

| $PLA_2$ | MAB <$PLA_2$> | $PGE_2$ [ng/ml] exp. 1 | exp. 2 | $LTC_4$ [ng/ml] exp. 1 | exp. 2 |
|---|---|---|---|---|---|
| type I | DSM ACC2026 | | | | |
| " | 0.01 mg/ml | 0.82 | 1.99 | 0.13 | 0.12 |
| " | 0.001 mg/ml | 0.97 | 1.73 | 0.14 | 0.14 |

EXAMPLE 6

The inhibition of the enzymatic activity of human duodenal phospholipase $A_2$ by the antibodies according to the invention and the antibodies deposited for EPA 0 287 387 was determined according to Example 3 of the invention.

The results are set forth in the following Table 3:

TABLE 3

| Antibody concentration µg/ml | % Inhibition | | | |
|---|---|---|---|---|
| | Invention DSM ACC2025 | Invention DSM ACC2026 | Prior art 1008-1 | Prior art 1085-2 |
| 10 | 93 | 94 | 68 | 88 |
| 1 | 86 | 88 | 11 | 36 |
| 0.1 | 56 | 56 | 3 | −2 |
| 0.01 | 16 | 20 | 3 | −9 |

Thus the antibodies according to the invention inhibit $PLA_2$ at a substantially lower concentration than the antibodies of the prior art.

EXAMPLE 7

The detection or determination of phospholipase $A_2$ can be carried out according to the procedure described in Example 2.1 of U.S. Pat. No. 5,244,789, the content of which is incorporated herein by reference in its entirety.

An assay carried out in a manner analogous to the assay set forth in U.S. Pat. No. 5,244,789, with the exception that it is performed in the presence of 100 µg/ml monoclonal antibody DSM ACC2025 or DSM ACC2026. The difference in the $PLA_2$ activities is the activity of type I phospholipase $A_2$.

In order to ensure that the enzyme activities measured in serum are not influenced by type I $PLA_2$, the following procedure may be applied: Sample material is subjected to pretreatment using an inhibitory antibody against type I $PLA_2$ (10 to 100 µg/ml; 15 minutes). This type I Mab does not affect the enzymatic activity of type II $PLA_2$ (see Table 4). Thereafter, the enzymatic activity can be determined according to known methods. This process prevents the misinterpretation of determination of type II $PLA_2$ activity, which misinterpretation is caused by type I $PLA_2$, and thus results in a substantial improvement over known detection methods.

TABLE 4

INHIBITION OF $PLA_2$-ACTIVITY BY MAK <$PLA_2$> 2.223.288 (IgG,k) (dose dependency)

| Dilution | Typ I $PLA_2$ | | Typ II $PLA_2$ | |
|---|---|---|---|---|
| | IgG | F(ab)$_2$ | IgG | F(ab)$_2$ |
| $10^{-1}$ | — | 92*⁾ | — | −3 |
| $10^{-2}$ | 82 | 83 | 0 | −1 |
| $10^{-3}$ | 77 | 66 | 0 | −3 |
| $10^{-4}$ | 66 | 37 | 0 | 10 |
| $10^{-5}$ | 39 | 8 | 0 | 5 |
| $10^{-6}$ | — | — | — | 4 |

IgG = 11.5 mg/ml
F (ab)$_2$ = 0.74 mg/ml
*⁾Inhibition in percent compared to control It is believed that other modifications may be made to the disclosure without departing from the spirit and scope of the invention. Furthermore, it is not intended that the present invention be limited to only the described embodiments. Modification of these embodiments will be recognized by those skilled in the art. Rather, the invention should be circumscribed by the scope of the appended claims.

We claim:

1. A pharmaceutical formulation comprising a monoclonal antibody which specifically binds type I phospholipase $A_2$ or a functional fragment of said antibody, wherein said monoclonal antibody is characterized as inhibiting at least 50% activity of said phospholipase $A_2$ at a concentration of less than 0.1 µg/ml, and an effective amount of a carrier substance, a filler, an auxiliary substance, or an additive.

2. Monoclonal antibody that specifically binds to a type I phospholipase $A_2$, wherein said antibody is characterized as inhibiting at least 50% phospholipase $A_2$ activity at a concentration of less than 100 ng/ml and is capable of binding in an equivalent manner to type I phospholipase $A_2$ as a monoclonal antibody obtainable from cell lines DSM ACC2026 or DSM ACC2025.

3. The monoclonal antibody of claim 2, wherein said antibody is obtainable from cell lines DSM ACC2026 or DSM ACC2025.

4. A cell line assigned DSM ACC2026.

5. A cell line assigned DSM ACC2025.

* * * * *

UNITED STATES PATENT AND TRADEMARK OFFICE
CERTIFICATE OF CORRECTION

PATENT NO. : 5,767,249
DATED : June 16, 1998
INVENTOR(S) : SCHEUER et al.

It is certified that error appears in the above-identified patent and that said Letters Patent is hereby corrected as shown below:

In column 5, line 49, Table 1, remove last number of last column, "26" and insert --20--.

In column 5, line 57, Table 1, after first "DSM" insert --ACC2025 or--.

Signed and Sealed this

Twentieth Day of June, 2000

Attest:

Q. TODD DICKINSON

*Attesting Officer*     *Director of Patents and Trademarks*